United States Patent [19]

Mak et al.

[11] Patent Number: 5,675,059
[45] Date of Patent: Oct. 7, 1997

[54] MOUSE LACKING THE EXPRESSION OF INTERFERON REGULATORY FACTOR 2 (IRF-2)

[75] Inventors: Tak W. Mak, Toronto, Canada; Tadatsugu Taniguchi, Osaka, Japan

[73] Assignee: The Ontario Cancer Institute, Toronto, Canada

[21] Appl. No.: 117,777

[22] Filed: Sep. 8, 1993

Related U.S. Application Data

[63] Continuation-in-part of Ser. No. 952,984, Sep. 29, 1992, abandoned.

[51] Int. Cl.$^6$ .......................... C12N 15/00; C12N 15/87; C12N 15/90; C12N 5/10
[52] U.S. Cl. .................. 800/2; 800/DIG. 1; 800/DIG. 3; 800/DIG. 4; 435/172.3; 435/240.2
[58] Field of Search .................... 800/2, DIG. 1, 800/DIG. 3, DIG. 4; 435/172.3, 240.2; 935/70, 52, 33, 34

[56] References Cited

PUBLICATIONS

D. Heinz et al, J. Mol. Biology ('94) vol. 236, pp. 869–886.
D. Schiffecli et al. J. Bacteriology, vol. 176 #4('94) pp. 1099–1100.
G. Moeck et al. J. Bacteriology, vol. 176 #14 ('94) pp. 4250–4259.
M. Teufel et al. EMBO J., vol. 12, #9, pp. 3399–3408.
G. Yamada et al. PNAS, vol. 88 (Jan. 1991) pp. 532–536.
H. Harada et al. Cell, vol. 58 (Aug. 25, 1989) pp. 729–739.
T. Mauiatis et al., *Molecular Cloning*, Cold Spring Harbor, N.Y., Cold Spring Harbor Laboratory Press 1982, pp. 270–279, 285–294, 310–312, 320–328.
E. Robertson Biology of Reproduction, vol. 44, ('91) pp. 238–245.

*Primary Examiner*—Charles C. P. Rories
*Attorney, Agent, or Firm*—Marshall, O'Toole, Gerstein, Murray & Borun

[57] ABSTRACT

The transcription factors, IRF-1 and IRF-2 are induced by interferons (IFNs) and a variety of other cytokines. IRF-1 functions as an activator whereas IRF-2 represses IRF-1 action by competing for binding to the same cis-elements. Recently, it has been shown that balanced expression between these two factors is critical for maintaining normal restraints on cell growth. Mutant mice deficient for IRF-2 were prepared by homologous recombination. In mutant cells, infection by Newcastle disease virus (NDV) resulted in the induction of type I IFN (IFN-α and IFN-β) mRNAs, the levels of which were significantly higher than in wild type cells; whereas, such a difference was not found upon induction by poly(I):poly(C). Unlike the IRF-1 deficient mutant mice, the IRF-2 deficient mice of the invention exhibit multiple phenotypes of physical vulnerability, including lethality to lymphocytic choriomeningitis virus (LCMV). Furthermore, in vitro colony formation assays have revealed a remarkable suppression of B cell lymphopoiesis in IRF-2 deficient mice.

4 Claims, 11 Drawing Sheets

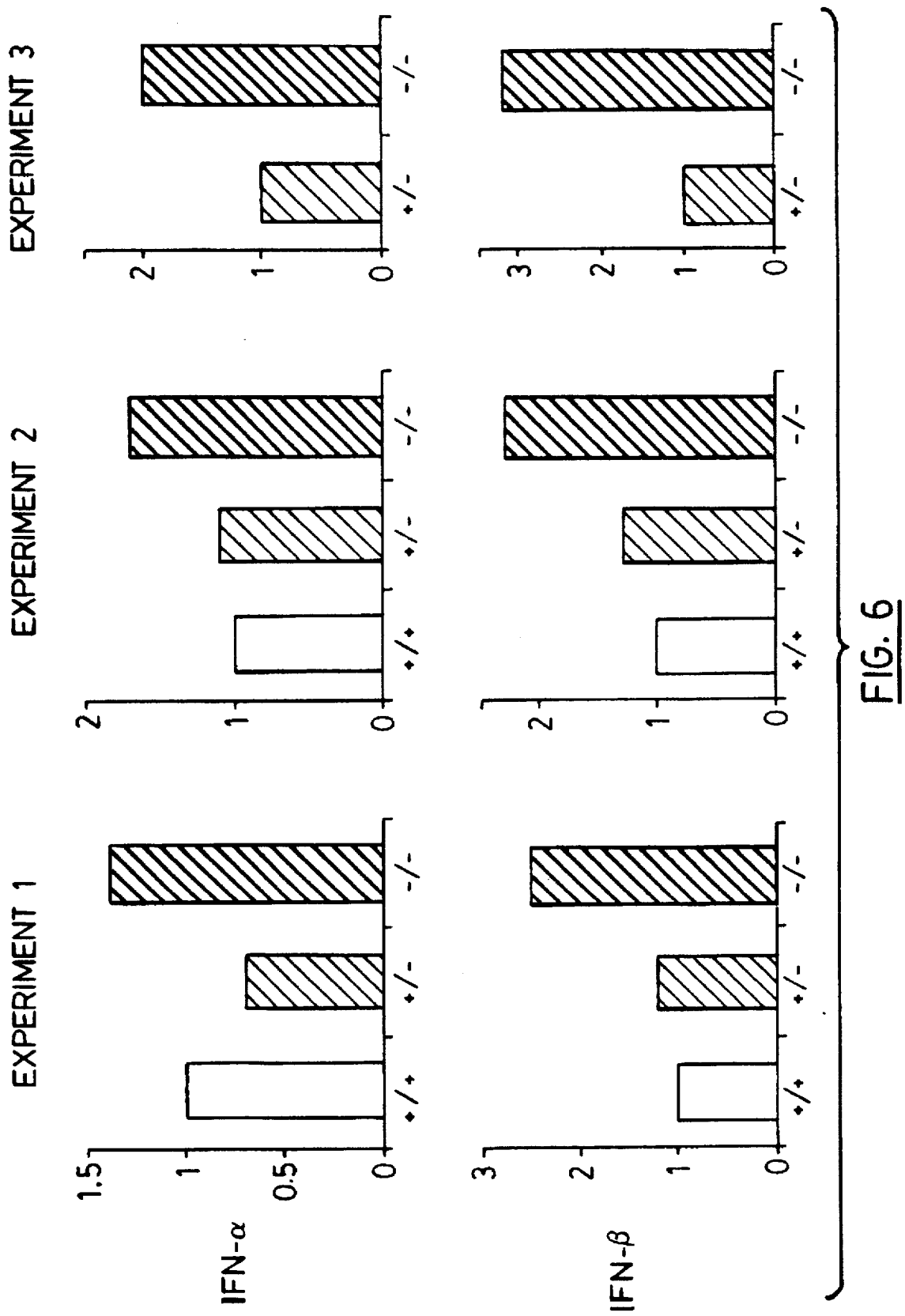

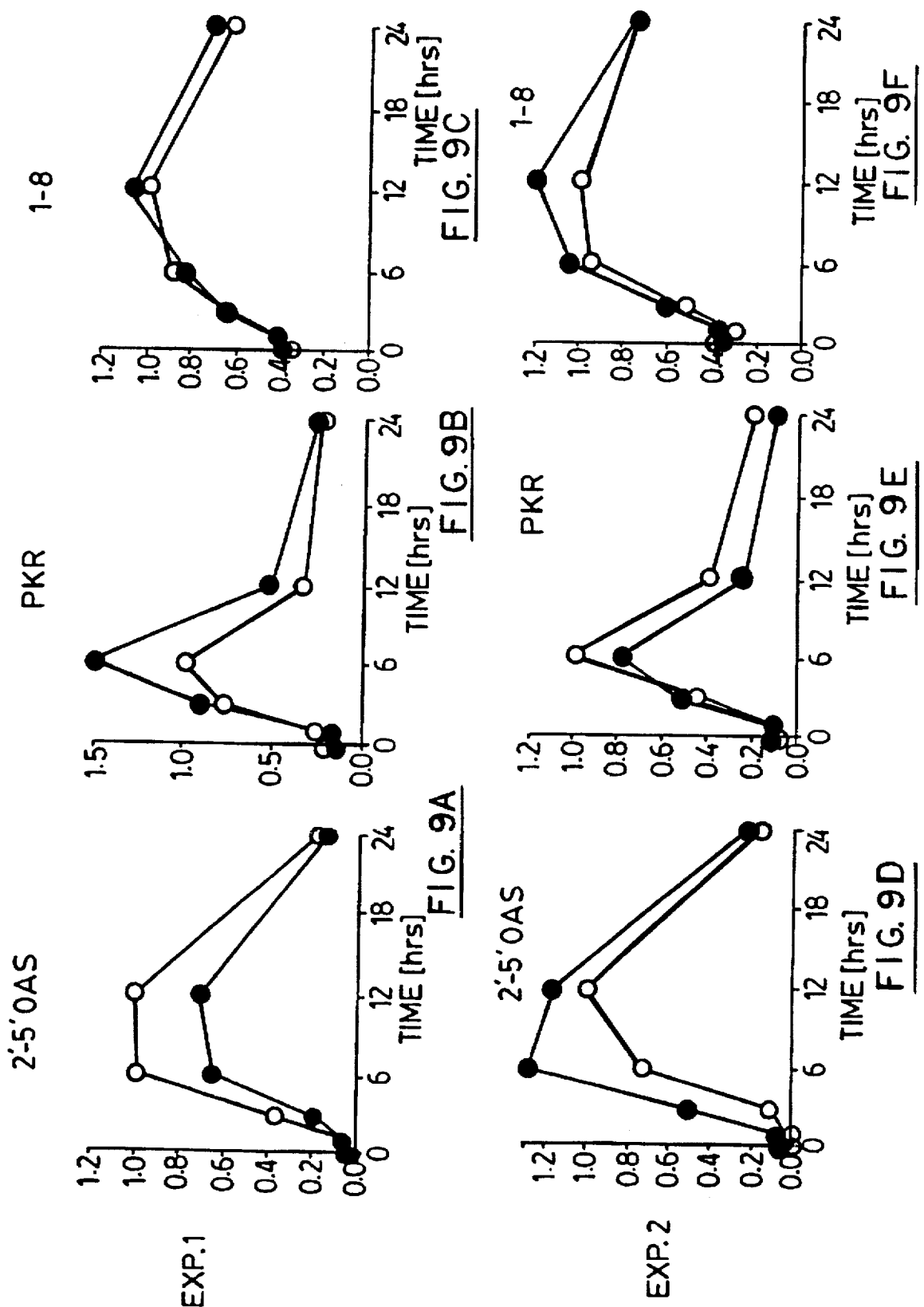

LCMV INFECTION INDUCES B CELL LYMPHOPENIA
AND ANEMIA IN IRF-2 DEFICIENT MICE

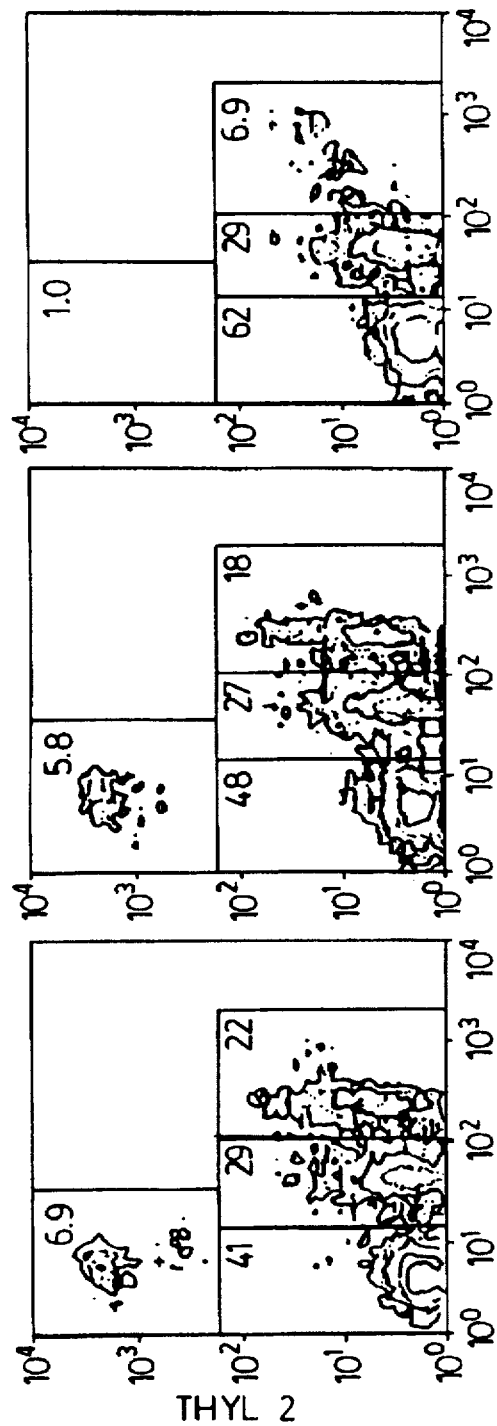
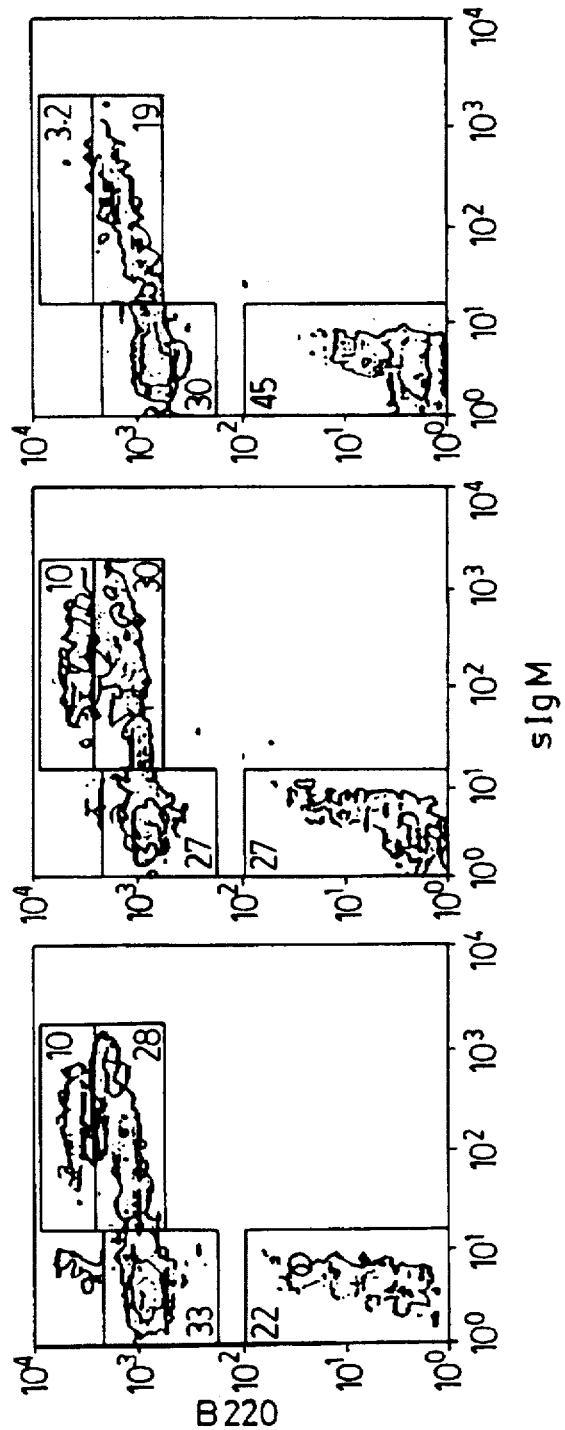
FIG. 15

MOUSE LACKING THE EXPRESSION OF INTERFERON REGULATORY FACTOR 2 (IRF-2)

CROSS-REFERENCE TO RELATED APPLICATION

This application is a continuation-in-part of application Ser. No. 07/952,984 filed Sep. 29, 1992, now abandoned.

BACKGROUND OF THE INVENTION

The invention is a mutant mouse lacking the expression of Interferon Regulatory Factor 2 (IRF-2). The invention is useful for the study of the response of the immune system to viral infection or other stimuli, and hence, for the development of treatments for viral diseases.

Type I interferons (IFNs; i.e. IFN-αs and IFN-β) are pleiotropic cytokines that are produced by many cell types in response to a variety of stimuli, such as, to viral infections, to double stranded RNA, e.g., Poly(rI):Poly(rC), and to some cytokines. On the other hand, Type II IFN, i.e. IFN-γ, is efficiently induced in T lymphocytes upon activation by antigens or by mitogens such as ConA and TPA (Stewart, 1979; Pestka et al., 1987; Weissmann and Weber, 1986; Vilcek, 1990). In addition to their potent anti-viral activity, IFNs also affect cellular growth and differentiation. In fact, IFNs exhibit anti-proliferative effects on many normal and transformed cells, suggesting that IFNs are "negative growth factors". IFNs are being used for the treatment of viral diseases and neoplasia. For example, IFNαs have been successfully used in the treatment of some types of leukemia (Palatanias and Ratain, 1991). IFNs bind to cell receptors to elicit their signals to cell interiors to induce a set of cellular genes, the so-called "IFN-inducible genes", thereby changing the physiology of the whole animal. The IFN-inducible genes include those of class I MHC (Israel et al., 1986; Sugita et al., 1987; Blanar et al., 1989; Korber et al., 1988) and 2',5'-oligoadenylate synthetase (Cohen et al., 1988). Cytokines transmit signals to the cell interior, resulting in the activation or repression of genes critical for cell growth and differentiation. Although the molecular mechanisms underlying cytokine-mediated cellular responses still remain obscure, recent studies have revealed the importance of transcription factors as the critical targets of cytokines. These factors, once induced or activated, regulate the expression of a variety of genes required for cytokine-induced cellular responses (Blank et al., 1992; Karin and Smeal, 1992; Marcu et al., 1992; Tanaka and Taniguchi, 1992).

Interferon Regulatory Factor-1 (IRF-1) and IRF-2, were originally discovered as transcriptional regulators for type I interferon (IFN) genes (Fujita et al., 1985, 1987, 1988; Miyamoto et al., 1988; Harada et al., 1989; MacDonald et al., 1990). DNA sequences recognized by IRFs have also been found in the IFN-stimulated regulatory elements (ISREs), of a number of IFN-inducible genes (Miyamoto et al., 1988; Harada et al., 1989; Pleiman et al., 1991; Tanaka et al., 1993). IRF-1 and IRF-2 can recognize the same DNA motifs, IRF-Es (G(A)AAA$^G/_C$$^T/_C$GAAA$^G/_C$$^T/_C$), through a highly conserved DNA binding domain (Tanaka et al., 1993). cDNA transfection studies have shown that IRF-1 functions as a transcriptional activator, and IRF-2 represses IRF-1 action (Fujita et al., 1989a; Harada et al., 1989, 1990; Näf et al., 1991; Reis et al., 1992). In addition, the genes for IRF-1 and IRF-2 are both virus- and IFN-inducible (Miyamoto et al., 1988; Harada et al., 1989; Pine et al., 1990). Collectively, these observations support the notion that IRFs may play a critical role in the regulation of the IFN system and host defense against virus infection.

In addition to IFN system regulation, the IRFs function more broadly in the regulation of cellular responses. In fact, expression of IRF-1 and IRF-2 is induced by other cytokines, hormones, and activators of second messenger pathways, implying that IRFs may also participate in the cellular responses to the following stimuli: interleukin-1 (IL-1), tumor necrosis factors (TNFs) (Fujita et al., 1989b), prolactin (Yu-Lee et al., 1990), interleukin-6 (IL-6), and leukemia inhibitory factor (LIF) (Abdollahi et al., 1991). More recently, it has been shown that overexpression of IRF-2 can transform NIH3T3 cells and concomitant expression of IRF-1 can suppress the transformed phenotype elicited by IRF-2 overexpression (Harada et al., 1993). In this context, the deletion and/or inactivation of the human IRF-1 gene, mapped to 5q31.1, has been found in human leukemia and preleukemic myelodysplasia (Willman et al., 1993). These observations support the idea that a proper balance between IRF-1 and IRF-2 may be critical for controlled cell proliferation and differentiation. From this point of view, it is interesting that transgenic mice expressing IRF-1 under the control of immunoglobulin-enhancer develop severe B cell lymphopenia (Yamada et al., 1991), and that anti-sense oligonucleotides for IRF-1 inhibit the cytokine-induced haematopoietic differentiation of a cultured cell line M1 (Abdollahi et al., 1991).

SUMMARY OF THE INVENTION

In the present invention, the IRF-2 gene has been inactivated by homologous recombination in mouse pluripotent embryonic stem (ES) cells which were then introduced into the mouse germline (Capecchi, 1989). In IRF-2 deficient cells, expression of type I IFN genes was up-regulated after infection by NDV. Furthermore, infection by LCMV resulted in lethality. The number of various bone marrow progenitors was significantly reduced in uninfected mutant mice, and anemia and more severe B cell lymphopenia were induced by LCMV infection. The results presented here further point to the importance of the balance between activator (IRF-1) and repressor (IRF-2) expression in IFN gene expression, host-defence against viral infection, and in the regulation of haematopoiesis.

The present invention is the generation of a mouse strain with null mutations in the IFN regulatory gene, IRF-2. This mouse strain will be an ideal model for the analyses of the expression of these transcriptional factors, IFNs and other genes that are affected by these genes. As well, the inducibility of IFNs, IRF-1 and IRF-2 genes after administration of IFNs or infection by viruses or other treatments will also establish the usefulness of these mice as animal models to study the roles of IFNs in development. Furthermore, these animals may be relevant systems to test the influence of IFNs in rejection of tumors and pathogen infections as well as in autoimmune diseases development.

BRIEF DESCRIPTION OF THE DRAWINGS

FIG. 6 shows the relative amounts of IFN-α and IFN-β mRNAs at peak time. Expression of IFN-α and IFN-β genes were monitored as described above. In three independent experiments, the mRNA levels at peak time (12 hr after infection) were quantitated by densitometry analysis and normalized by β-actin. The expression levels of wild type (experiments 1 and 2) or heterozygous (experiment 3) fibroblasts were assigned the value of 1.0 in each graph.

FIGS. 9A–9F show the relative amounts of 2'-5' OAS (9A–9B), PKR (9C–9D) and 1–8 (9D–9F). Expression levels were monitored as described above. In two independent experiments, the mRNA levels were quantitated using an imaging analyzer (BAS2000, Fuji Inc.) and normalized by β-actin. The expression levels of heterozygous fibroblasts were assigned the value of 1.0 in each graph. Open and filled circles indicate the values of heterozygous and homozygous fibroblasts, respectively.

FIG. 15 shows flow cytometric analysis of lymphocytes in bone marrow. Bone marrow cells from mice with each genotype were analyzed by two color flow cytometry. Antibodies used were anti-Thy1.2 (53-2.1), anti-B220 (RA3-6B2) and anti-sIgM (R-40-97). The percentages of cells in relevant regions are indicated.

In preparation for in vitro and in vivo studies of the role of type I interferons in normal and disease situations, animals that contain mutations in the genes of IRF-2 were generated. The animal species used was mouse since mice have become the preferred animal for use in disease studies as the mouse immune system closely resembles that of the human. The strategy for obtaining mice having mutated IRF-2 genes involved manipulation of the genes of the transcriptional factors rather than the genes of the interferons themselves. One reason for taking this approach was that there are multiple copies of the type I interferon genes, which obviously make it difficult to create mutations in all of them (Stewart, 1979; Weissman and Weber, 1986; Pestka et al., 1987; Vilcek, 1990). For another reason, this approach allows for the dissection of the functions of each of the two interferon response factors. Following this strategy mutant mouse strains carrying null mutations of the gene of IRF-2 were created.

DESCRIPTION OF THE PREFERRED EMBODIMENTS

Generation of Mice with Homozygous Mutation in the IRF-2 Gene

Figure 1:
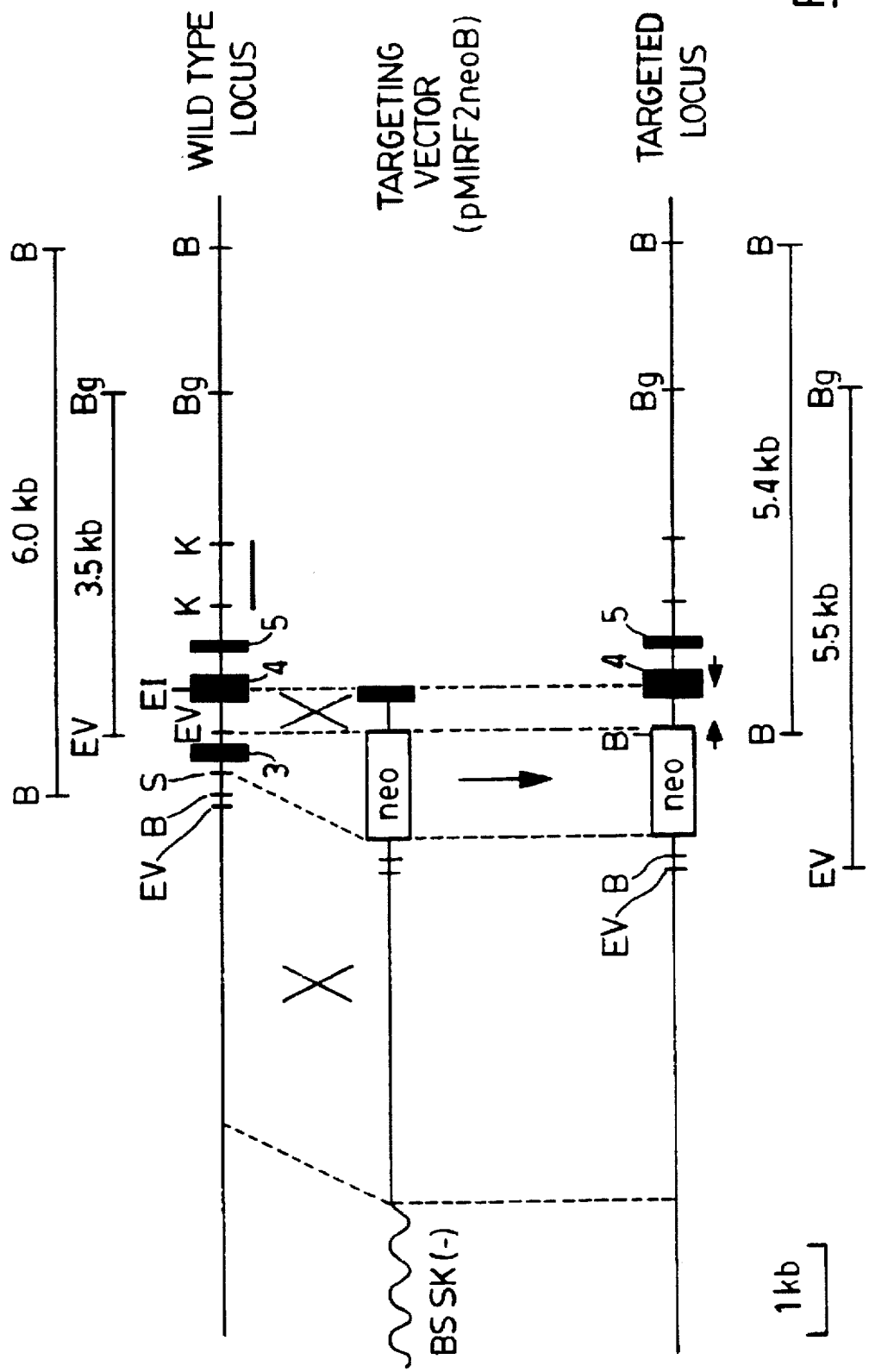
FIG. 1 is a schematic diagram of the targeting strategy of the IRF-2 gene. Black boxes represent exons 3 and 4. B, Bg, EI, EV, K and S represent cleavage sites for BamHI, BglII, EcoRI, EcoRV, KpnI and SalI, respectively in the wild type locus. For targeting vector pMIRF2neoB, the wavy line indicates pBluescript SK(+) plasmid sequence. The neo$^r$ gene is derived from pMC1neoPolA (Thomas and Capecchi, 1987). The predicted structure of the mutated IRF-2 allele following homologous recombination is shown at the targeted locus. Arrows indicate oligonucleotides used for PCR analysis.

IRF family proteins have a highly conserved DNA binding domain within their amino-terminal 120 amino acids (Harada et al., 1989, Driggers et al., 1990, Veals et al., 1992, Uegaki et al., 1993). To introduce a targeted mutation into the IRF-2 gene, a targeting vector, pMIRF2neoB, was constructed which has the deletion in the third exon encoding part of the DNA binding domain (from amino acids 30 to 63) (FIG. 1). Even if splicing were to occur between the second exon (spanning from the 5'-untranslated region to amino acids 29) and the fourth exon (from amino acids 63 to 121), a nonsense protein will be produced by a frameshift after amino acid 30. Thus, in any event, IRF-2 should be functionally inactivated after homologous recombination.

Figure 2:
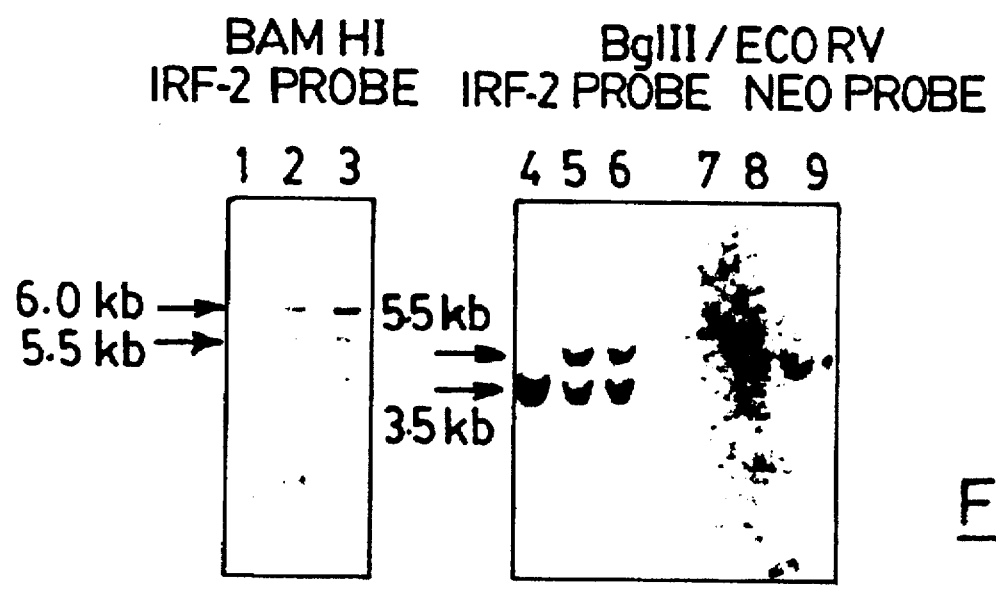
FIG. 2 shows Southern blot analysis of DNA from ES clones containing a mutated allele. Ten micrograms of DNA from parental ES cells (lanes 1, 4 and 7) and from two representative targeted clones (lanes 2, 3, 5, 6, 8 and 9) was digested with BamHI (lanes 1–3) or BglII/EcoRV (lanes 4–9) and subjected to Southern blot analysis using the probe shown in FIG. 1 (black bar) (lanes 1–6) or a neomycin probe (lanes 7–9). The 5.5 kb band for BamHI and the 5.5 kb band for BglII/EcoRV represent mutated alleles.
Figure 3:
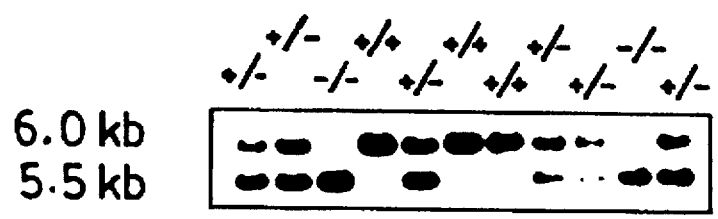
FIG. 3 shows Southern blot analysis of tail DNA of a litter derived from a heterozygous mating pair.

The construct pMIRF2neoB was introduced into D3 embryonic stem cells (Doetschman et al., 1985) by electroporation. To identify homologous recombination events, a rapid sib-selection method using the polymerase chain reaction (PCR) (Joyner et al., 1989) was chosen. The results were then confirmed by genomic Southern blot analysis (FIG. 2). The average frequency of homologous recombination was approximately 1 in 500 G418$^r$ cells or 1 in $1.4 \times 10^7$ electroporated cells. Germline transmission of the mutation occurred in mice representing two independent ES cell lines. Heterozygous mice were interbred to obtain mice homozygous for the mutated IRF-2 allele. Progeny were analyzed for genotype 4-6 weeks after birth, and it was found that 32% (39/121), 45% (56/121) and 22% (26/121) of pups were wild type, heterozygous and homozygous, respectively (see FIG. 3; data not shown). Gender distortion was not observed. Heterozygous and homozygous mice showed no apparent abnormalities in their reproductive ability and behavior. However, physical vulnerability of the IRF-2 deficient mice has been consistently observed; they die more frequently at a relatively young age as compared to wild type mice. 38% of the homozygous mutant mice died within 8 months after birth, whereas 12% of wild type mice died within same period (data not shown). Females often died after giving birth. Old mice often showed erosions and ulcers around the neck, back and abdomen, which, in severe cases, resulted in patchy scars and post-inflamatory hair loss (data not shown).

Figure 4:
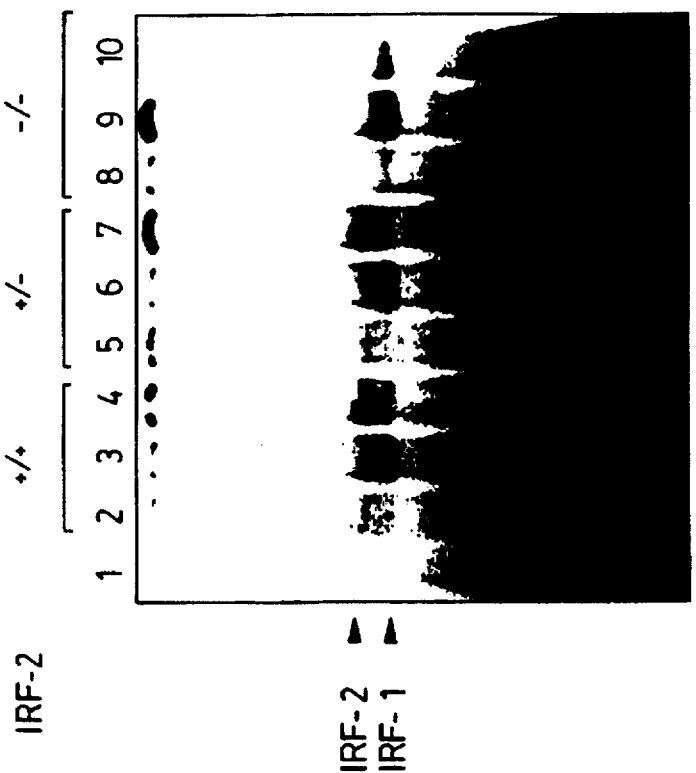
FIG. 4 shows gel shift analysis of IRF-2. Whole cell extracts were prepared from IFN-β-, NDV- or mock-induced embryonic fibroblasts from each genotype (lanes 2–4, wild type fibroblasts; lanes 5–7, fibroblasts with the heterozygous mutation; lanes 8–10, fibroblasts with the homozygous mutation). Gel shift analysis was carried out using 10 µg of cell extracts (lane 1, no extract; lanes 2, 5 and 8, untreated cell extracts; lanes 3, 6 and 9, IFN-β-treated cell extracts; lanes 4, 7 and 10, NDV-infected cell extracts) and 5 fmol of $^{32}$P-labeled C1 oligomer (Fujita et al., 1987) as the probe. Arrowheads indicate the positions of the factor-DNA complex.

To confirm that the IRF-2 gene is inactivated in the homozygous mice, gel shift analysis was carried out using cell extracts prepared from mock-induced, IFN-treated or Newcastle disease virus (NDV) infected embryonic fibroblasts. In wild type, heterozygous and homozygous fibroblasts, activity of IRF-1 was inducible after NDV infection or IFN-β induction. However, activity of IRF-2 could be detected only in wild type and heterozygous embryonic fibroblasts and not in homozygous mutant fibroblasts (FIG. 4).

Induction of Type I IFN Genes in IRF-2 Negative Cells

Figure 5:
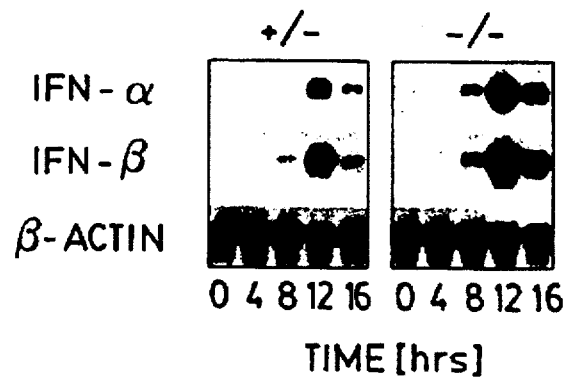
FIG. 5 shows induction of IFN-α and IFN-β genes by NDV. Embryonic fibroblasts were prepared from littermate embryos of heterozygous mating pairs. Five micrograms of total cellular RNA, isolated at the indicated time after NDV infection (Fujita et al., 1985), were subjected to Northern blot analysis. The filters were re-probed with β-actin after probing with IFN-α and IFN-β. Representative results are shown (Experiment 3 in FIG. 6).

IRF binding sites (IRF-Es) are present in the promoters of IFN-α and IFN-β genes. Gene transfection studies in the IRF-negative embryohal carcinoma cell line P19 have revealed that IRF-2 can repress the transcriptional activation of the IFN-β gene promoter by IRF-1 (Harada et al., 1990). To investigate whether expression of type I IFN genes is affected by the absence of IRF-2, the levels of IFN-α and IFN-β mRNAs upon viral infection of wild type, heterozygous and homozygous mutant cells was examined. Embryonic fibroblasts prepared from littermate embryos of heterozygous mating were infected by NDV, and mRNA levels of IFN-α and IFN-β were monitored by Northern blot analysis. IFN-α and IFN-β mRNAs were undetectable in homozygous mutant fibroblasts prior to viral infection (FIG. 5), indicating that the lack of the repressor IRF-2 does not cause IFN gene expression. Upon infection by NDV, expression levels of IFN-α and IFN-β genes gradually increased, with mRNA levels peaking at 12 hr after infection in both wild type and mutant fibroblasts. Thereafter, IFN mRNA expression levels decreased with the same kinetics in both wild type and homozygous mutant fibroblasts. Interestingly, the relative amounts of mRNA at the peak time were consistently elevated 2-3 fold in homozygous mutants when compared to wild type or heterozygous mutant fibroblasts (FIG. 6). In addition, IFN activity was increased to a similar extent in culture supernatant of NDV-infected homozygous fibroblasts (data not shown). Similarly, increased type I IFNs mRNA in peritoneal macrophages after NDV infection was detected (data not shown).

Figure 7:
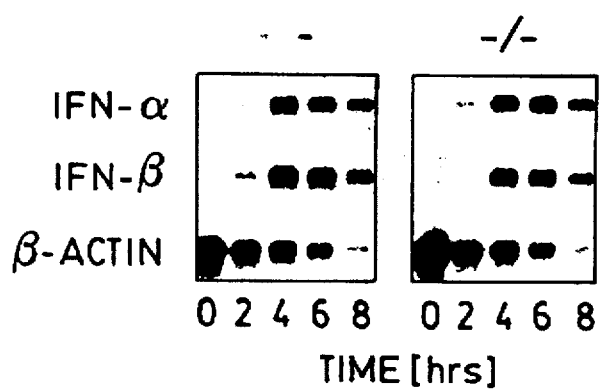
FIG. 7 shows induction of IFN-α and IFN-β genes by poly(I):poly(C). Embryonic fibroblasts were induced with poly(I):poly(C)(100 µg/ml, Yamasa Shoyu) in the presence of DEAE-dextran (500 µg/ml) for 1 hr. Five micrograms of total cellular RNA, isolated at the indicated time after poly(I):poly(C) induction, were subjected to Northern blot analysis. The filters were re-probed with β-actin after probing with IFN-α and IFN-β.

In addition to virus infection, type I IFNs are known to be induced by synthetic double stranded RNAs such as poly (I):poly(C). Unlike NDV infection, mRNA levels for IFN-α and IFN-β were essentially the same between the wild type and homozygous mutant fibroblasts, when induced by poly (I):poly(C) (FIG. 7).

IFNs elicit cellular responses by inducing a series of genes, the so-called "IFN-inducible genes". Many of them also have IRF-Es which overlap with ISREs of these genes (Tanaka et al., 1993). The induction of the following IFN-inducible genes was examined: 2'-5' oligoadenylate synthetase (2'-5' OAS), 1-8 and p65 double-stranded RNA-dependent protein kinase (PKR). As for the 2'-5'OAS gene, the IRF binding site has already been identified within the promoter (Tanaka et al., 1993).

Figure 8:
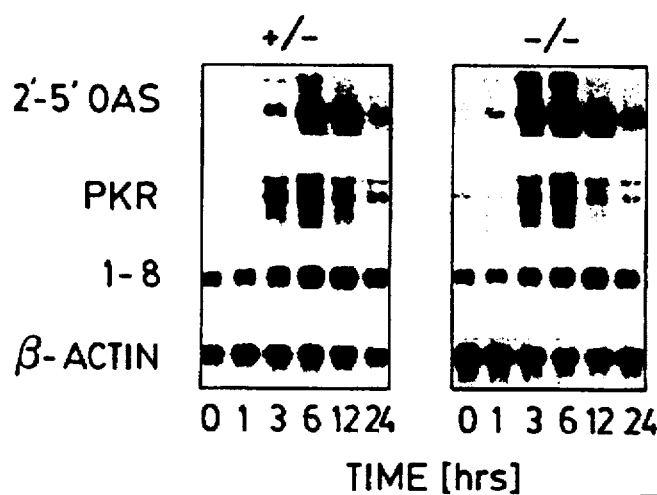
FIG. 8 shows induction of 2'-5' oligoadenylate synthetase (2'-5'OAS), p65 double stranded RNA-dependent protein kinase (PKR) and 1–8 genes. Embryonic fibroblasts were treated with IFN-β ($10^3$ IU/ml). Five micrograms of total RNA, isolated at the indicated times, were subjected to Northern blot analysis. The filters were re-probed with β-actin after probing with 2'-5'OAS, PKR and 1–8. Representative results are shown (Experiment 2 in FIGS. 9A–9F)

Embryonic fibroblasts were periodically harvested after IFN-β stimulation and mRNA levels of these IFN-inducible genes were determined by Northern blot analysis. As shown in FIGS. 8 and 9, basal expression levels, the time course of induction, and expression levels at the peak time of these genes were not affected in fibroblasts with the homozygous mutation in IRF-2.

Immune Response of IRF-2 Deficient Mice Against LCMV Infection

Figure 10:
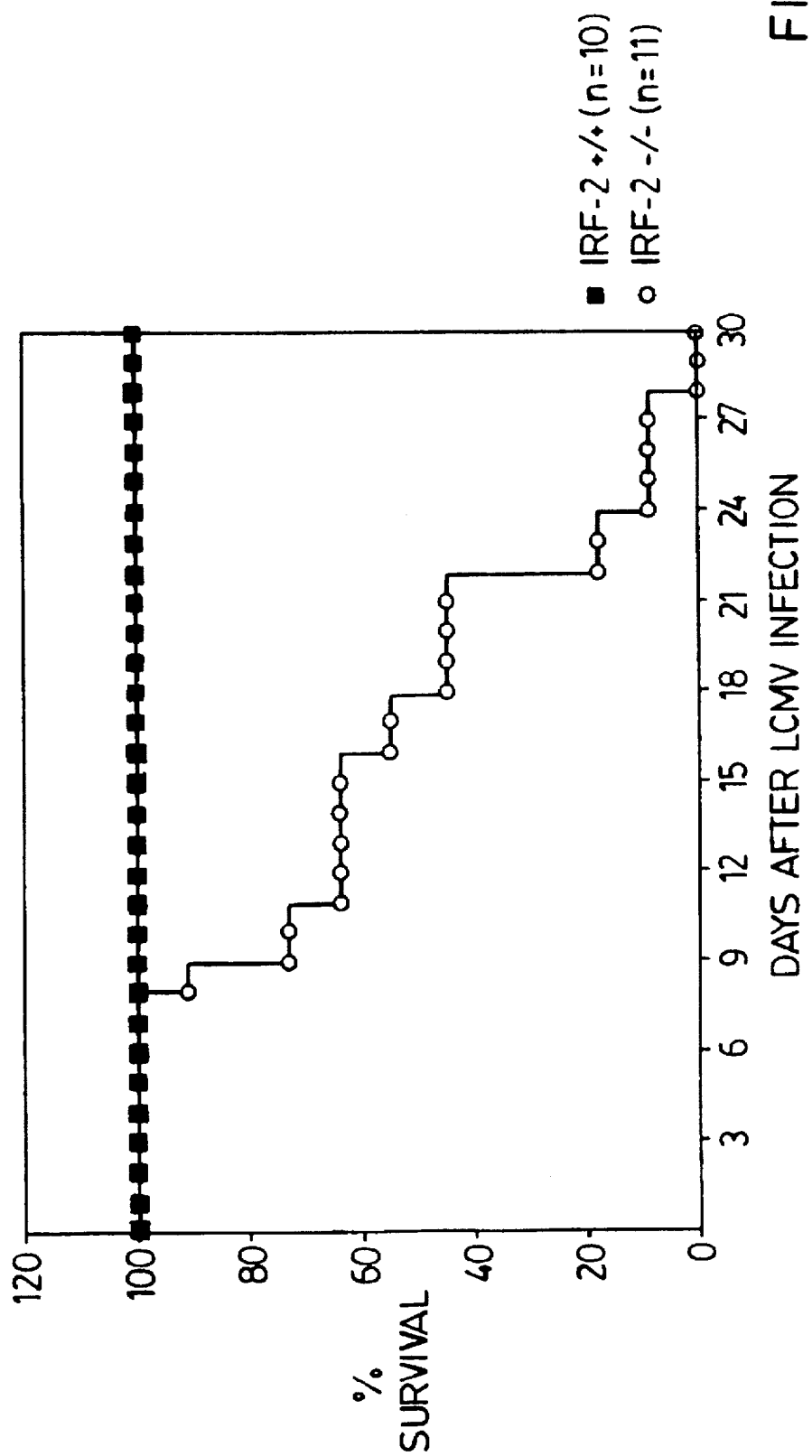
FIG. 10 shows a graph of the mortality of wild type (n=10) and homozygous mice (n=11) which were intravenously infected with LCMV (200 pfu). Percent survival was calculated as percentage of surviving mice per total infected mice. When moribund mice were expected not to survive until next day, they were sacrificed at the indicated days. Filled squares and open circles indicate the values of IRF-2 wild type and homozygous mutant mice, respectively.

To examine further the effect of IRF-2 deficiency on host defences, the susceptibility of IRF-2 deficient mice to virus infection was examined. Mice were intravenously challenged with LCMV (Armstrong strain). Surprisingly, IRF-2 deficient mice were dead or moribund within 4 weeks of infection, whereas wild type and uninfected mutant mice remained healthy under the same experimental conditions even after more than 1 month (FIG. 10).

Figure 11:
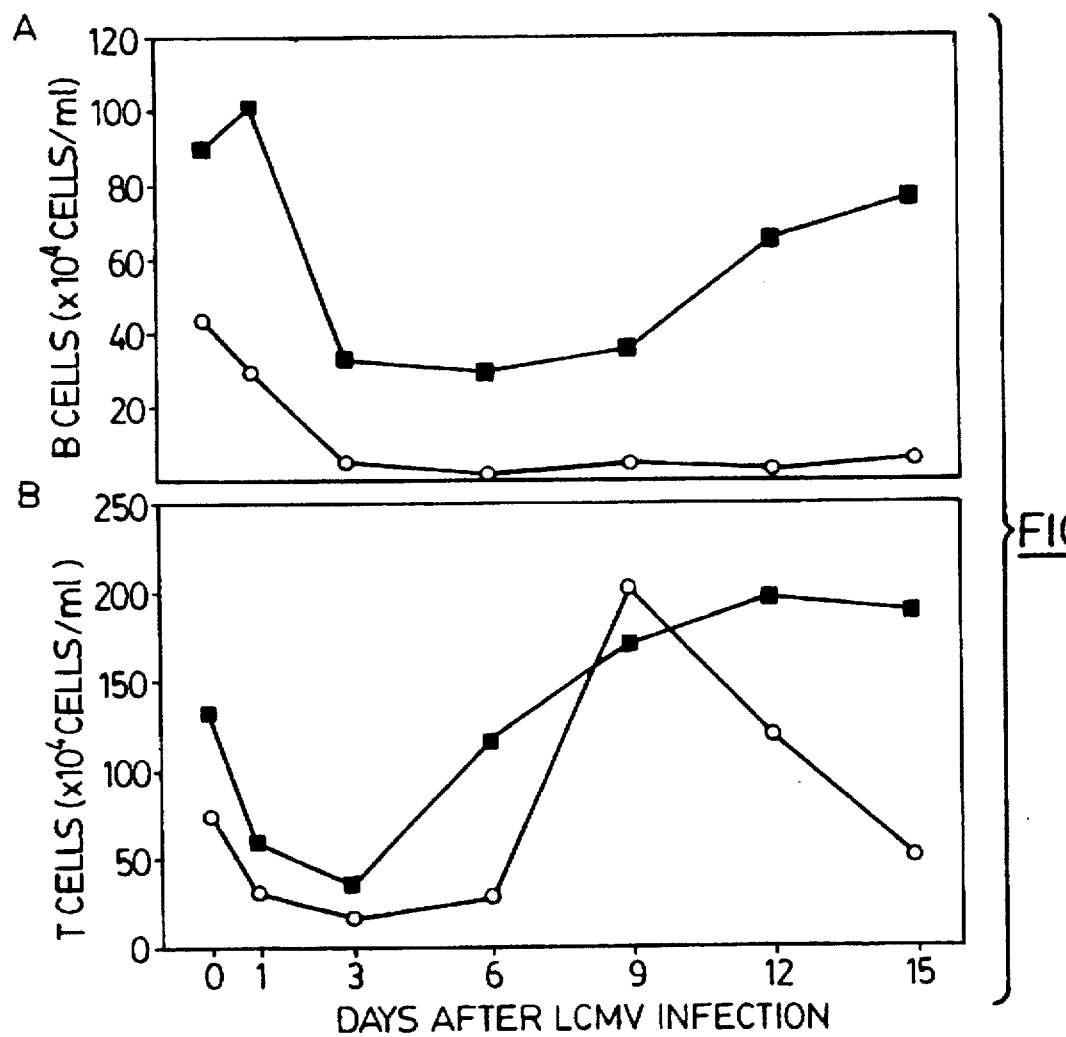
FIG. 11 shows changes of lymphocytes population after LCMV infection. LCMV (200pfu) was intravenously inoculated into 6 to 18 week old IRF-2 wild type and homozygous mutant mice. Peripheral blood was periodically collected to monitor changes in lymphocytes populations by flow cytometry analysis using anti-B220 antibody (A; RA3-6B2) and anti-CD3 e-chain antibody (B; 145-2C11). Absolute cell number was calculated as (total white blood cell number/ml)×(percentage of B220$^+$ or CD3$^+$ cells). The number of white blood cells was counted after treating blood with Turk's solution. Values for representative mice are shown. Filled squares and open circles indicate the values of IRF-2 wild type and homozygous mutant mice, respectively. The homozygous mutant mice often, but not always, showed lower numbers of white blood cells in peripheral blood.

In order to gain insights on the unusual susceptibility of mutant mice to LCMV, changes in lymphocyte populations in infected mice by flow cytometry were examined. An initial transient reduction in the number of lymphocytes was observed in peripheral blood of infected normal mice (FIG. 11). Interestingly, the reduction was enhanced and prolonged in IRF-2 deficient mice. The number of B cells in peripheral blood was gradually reduced to a level of less than 10% of wild type mice, and remained at a low level until death. On the other hand, the number of T lymphocytes, especially $CD8^+$ T cells, began to increase after day 3 as in normal animals. After day 9, however, the number of T cells began to decrease unlike wild type mice. In addition to peripheral blood, the number of splenocytes was also decreased at day 8 to less than 25% of normal mice.

Figure 13:
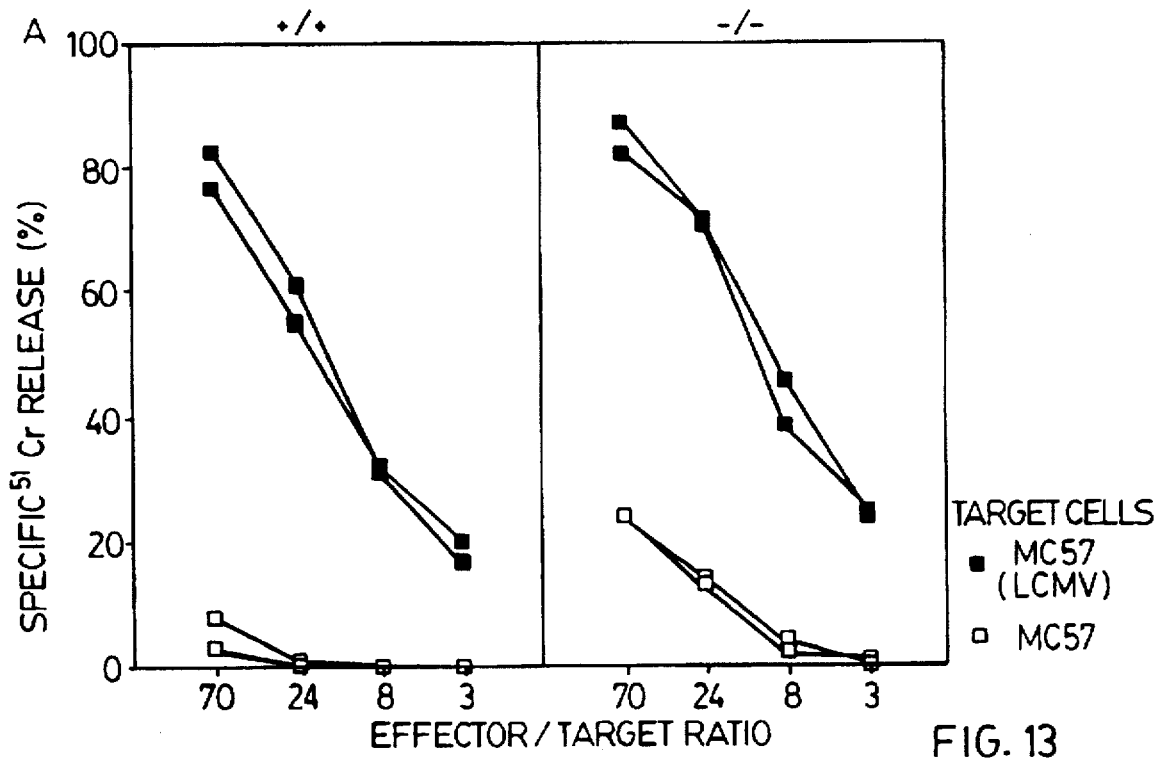
FIG. 13 shows cytotoxic T-lymphocyte activity of IRF-2 deficient mice. Mice were sacrificed at day 8 after i.v. infection of LCMV (200 pfu). CTL activity specific for LCMV was measured by a $^{51}$Cr release assay using the same numbers of splenocytes. Target cells were LCMV-infected (filled squares) or uninfected (open squares) MC57G fibrosarcoma cells.
Figure 14:
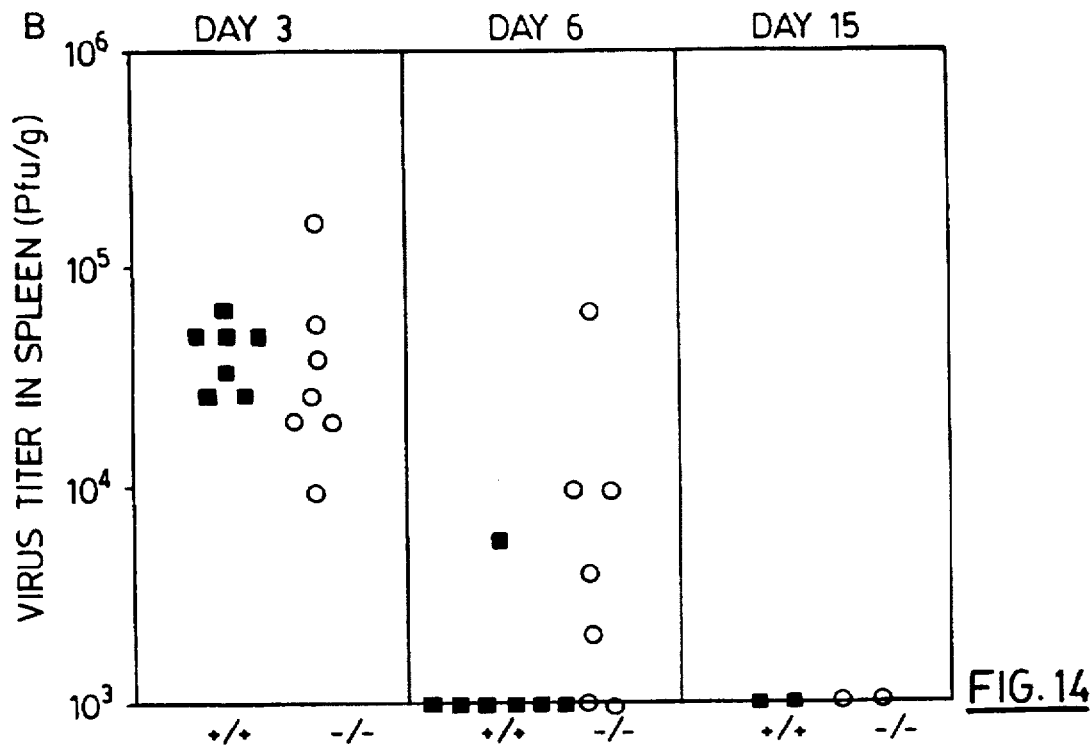
FIG. 14 shows spleen virus titer. Spleen homogenates were prepared from mice at day 3, 6 and 15 after inoculation. Virus titer was determined by the plaque forming assay as described in Experimental Procedures. Filled squares and open circles indicate the values for wild type and homozygous mice, respectively.

LCMV inoculated via extraneural routes is usually cleared by LCMV-specific cytotoxic T lymphocytes (McChesney and Oldstone, 1987). In order to determine whether IRF-2 deficient mice could generate an immune response against LCMV, the cytotoxic T cell (CTL) function specific for LCMV was examined. As shown in FIG. 13, mutant mice showed normal CTL activities against LCMV-infected or LCMV derived peptide loaded target cells (data not shown), indicating that CTL activation occurred normally. In addition, IRF-2 deficient mice could clear LCMV as monitored by a plaque forming assay (FIG. 14). Finally, LCMV in moribund and postmortem mutant mice could not be detected (data not shown). These results indicate that IRF-2 deficient mice could mount immune responses and clear LCMV.

Figure 12:
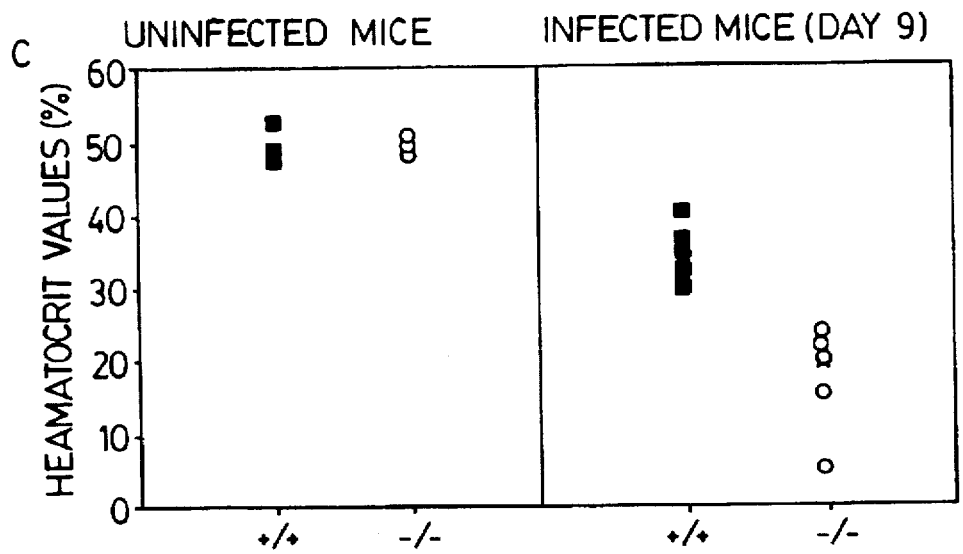
FIG. 12 shows haematocrit values before and after LCMV infection. At day 9 after infection, haematocrit values were examined by conventional method using centrifugation. Filled squares and open circles indicate the values of wild type and homozygous mice, respectively.

During the course of infection studies, a dramatic reduction of haematocrit values in some infected IRF-2 deficient mice was found (FIG. 12). Wild type and mutant mice showed comparable haematocrit values before infection (about 50%), but after infection, their values were decreased in both strains, with the reduction being more pronounced in IRF-2 deficient mice. In fact, some IRF-2 deficient mice suffered from severe anemia (haematocrit values of 5–10%) before death. In other mutant mice, haematocrit values gradually increased to approximately 30% but the mice died before the values reached basal levels. In wild type mice, haematocrit values returned to basal levels within 2 weeks.

Haematopoiesis in IRF-2 Deficient Mice

Figure 16:
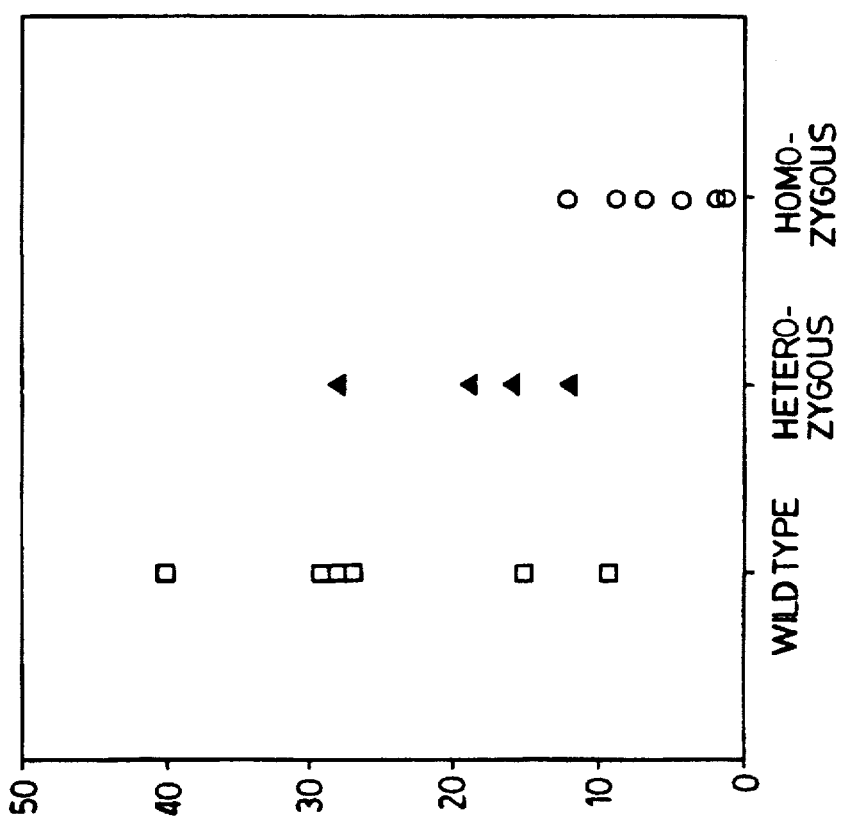
FIG. 16 shows lymphocytes in peritoneal exudate cells. Peritoneal cells were analyzed by flow cytometry using anti-Thy1.2 (53-2.1) and anti-B220 (RA3-6B2). Percentages are expressed as (Thy1.2$^+$ cells+B-220$^{30}$ cells)/(total peritoneal cells)×100.

In view of the dramatic alterations in haematopoietic populations after LCMV infection, it is possible that IRF-2 deficient mice have certain defects in haematopoiesis. Therefore, haematopoietic populations in various lymphoid organs of uninfected mice were analyzed. Gross inspection of the lymphoid organs (thymus, lymph nodes, and spleen) of homozygous mutant mice revealed no signs of abnormalities. Extensive flow cytometric analyses with a panel of monoclonal antibodies against T and B cell markers revealed no apparent changes in thymus, lymph node, and spleen cell populations (data not shown; see the Experimental Procedures as to antibodies tested). However, in the bone marrow of homozygous mice, the number of $Thy1^+$ cells was reduced to 20–50% of wild type and heterozygous mice (FIG. 15). This population is considered to be mature $TcR\alpha\beta^+$ T cells because the $TcR\alpha\beta^+$ cell population was correspondingly reduced in the bone marrow (data not shown). As well, a decreased number of $B220^{high}/sIgM^+$ cells was observed in bone marrow, a population, which includes newly generated mature B cells and mature B cells that return from the periphery (30–70% of wild type and heterozygous mice; FIG. 15). There was also a reduction in the number of lymphocytes in the peritoneal exudate cells (FIG. 16). It should be noted that, unlike IRF-1 deficient mice, which show a specific defect in development of $CD8^+$ T lymphocytes, IRF-2 deficient mice have normal numbers of $CD4^+$ and $CD8^+$ T lymphocytes in all lymphoid organs (data not shown).

Reduced Bone Marrow Function in IRF-2 Deficient Mice

Figure 17:
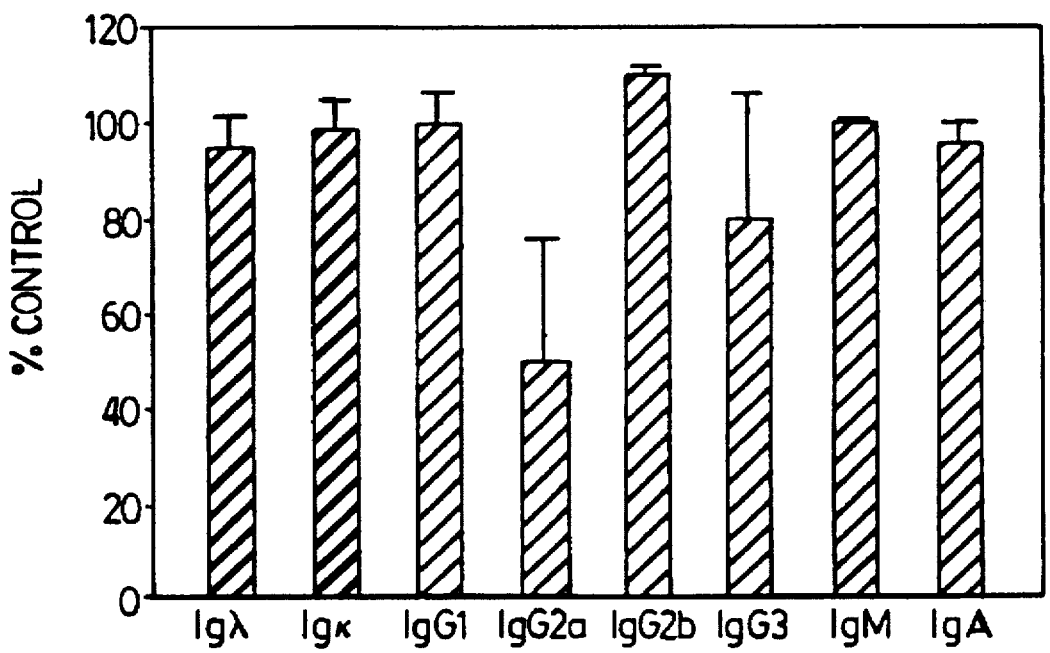
FIG. 17 is a graph showing immunoglobulin isotypes. Immunoglobulin isotypes were examined by ELISA using isotype specific antibodies (BioRad). Percentage of optical density (405, 620 nm) versus control is expressed as mean ±S.D. (standard deviation) of 3 independent experiments. Wild type and heterozygous mice did not show any differences.

In order to study the haematopoietic abnormality in IRF-2 deficient mice, levels of serum immunoglobulin isotypes were analyzed. As shown in FIG. 17, there was a significant reduction in IgG2a levels in homozygous mutant mice.

Figure 18:
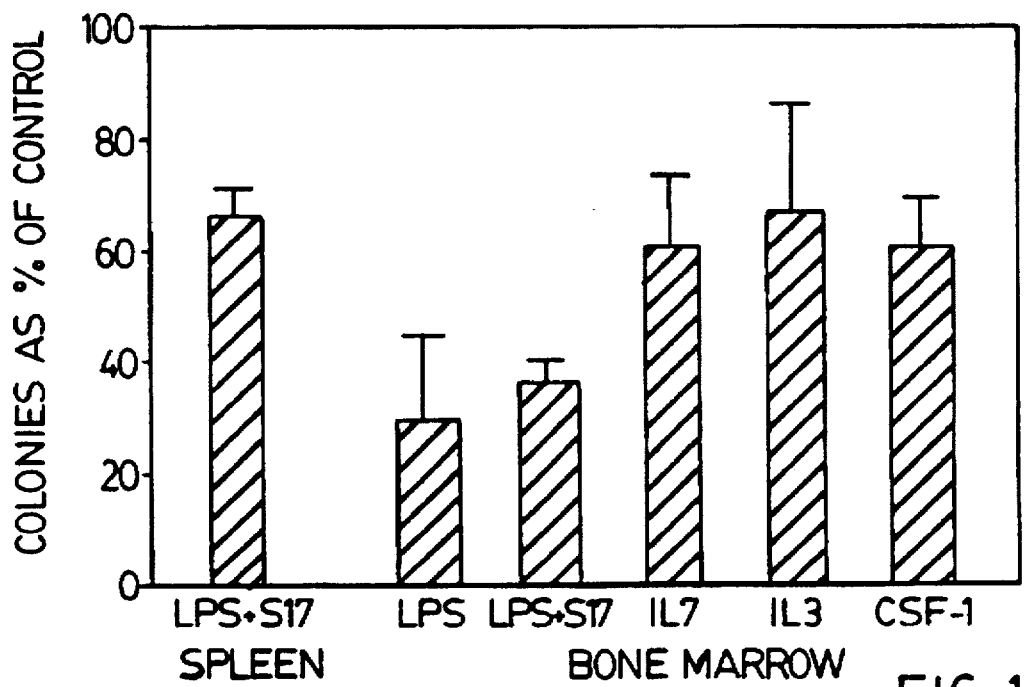
FIG. 18 is a graph showing results of colony formation assay. Colony formation in agar containing various stimulators was scored. Responding cells to LPS, IL-7, IL-3 and CSF-1 are mature B cells, pre-B cells, multipotential progenitors and macrophage precursors, respectively. Percentage of colonies versus control mice is expressed as mean ±S.D. of 3 independent experiments. Wild type and heterozygous mice did not show any differences.

Bone marrow cells were assayed for their ability to form colonies in agar containing a variety of stimulators in the presence or absence of the stromal cell line S17 (FIG. 18). Bone marrow cells with the homozygous mutation showed a dramatic decrease in colony formation in response to the B cell mitogen LPS (70% reduction when compared to wild type and heterozygous mice). These colonies correspond to mature B cells. Splenocytes of homozygous mice also showed reduced number of colonies responsive to LPS (30% reduction). In addition, reduced colony formation of bone marrow cells in response to several cytokines including IL-3, IL-7 and CSF-1 (approximately 40% reduction was observed). The cells responding to these cytokines are multipotential progenitors, pre-B cells, and macrophage precursors, respectively. These results indicate that B cell haematopoiesis in bone marrow is dramatically altered in the absence of IRF-2.

Discussion

IRF-2 has been extensively studied, together with IRF-1, in the context of IFN system regulation. The present invention provides a mutant mouse lacking the expression of IRF-2. Using cells lacking IRF-2, induction of type I IFN and some IFN-inducible genes was examined. Peak induction of type I IFN mRNAs was consistently enhanced in NDV-infected homozygous mutant fibroblasts and macrophages. In contrast, no difference was seen between wild type and mutant fibroblasts with induction by poly(I):poly(C). In this regard, it is interesting to note that embryonic fibroblasts from IRF-1 deficient mice show a dramatic decrease in IFN mRNA induction by poly(I):poly(C), whereas no such difference was seen when the same cells were induced by NDV, suggesting the existence of IRF-1 dependent and independent mechanisms for IFN gene induction. How are these observations reconciled? It is possible that in IRF-2 deficient cells the IRF-1 independent mechanism(s) will also operate upon NDV infection. Since IRF-1 is induced in these cells by NDV, IRF-1 can also contribute to IFN gene induction in the absence of IRF-2. In fact, it has been shown previously that IRF-1 can activate type I IFN promoters in IRF-2 negative embryonal carcinoma cell line P19 (Harada et al., 1990). Thus, it is plausible that the observed upregulation of IFN gene induction by NDV may be a reflection of these mixed events. On the other hand, in poly(I):poly(C)-induced cells the IRF-1 dependent, but not the independent mechanism, would operate. With the existence of other factors, PRDI-BF and ICSBP, that bind PRD-I domain and have repressor activity in the induction of type I IFN (Keller and Maniatis, 1991; Weisz et al., 1992; Nelson et al., 1993), there is evidence for considerable redundancy in the regulation of type I IFN. Obviously, further clarification will be required on this issue, but it can be concluded from these experiments that the mechanism of type I IFN induction is more complicated than previously proposed.

As shown in FIGS. 8 and 9A–9F, the induction of 2'-5'OAS, PKR, and 1–8 genes by IFN-β was not significantly altered in embryonic fibroblasts lacking IRF-2. In view of previous results showing that IRF-2 can repress IRF-1 action (Harada et al., 1989, 1990), one might have envisaged an upregulation of IFN-inducible genes following the induction of such IRF-2 negative cells by IFNs. Although there is no clear explanation at present, the activation of ISREs is also mediated by a factor(s) other than IRF-1 such as ISGF3 (or factor E). It has been suggested that IRF-1 may play a role in maintaining transcription initiated by ISGF3 (factor E), and that dependency on a given factor is determined by the sequence of and around ISREs (reviewed in Stark and Kerr, 1992). Hence, whatever the mechanism, it is clear that the ISREs of the above three genes are not significantly affected by IRF-2. On the other hand, in view of the present observation that the lack of IRF-2 leads to suppression of haematopoiesis, the existence of yet unidentified genes involved in the regulation of hematopoiesis which may be dramatically affected by the absence of IRF-2 may be inferred (see below). The complexity of IFN-mediated gene regulation may be accounted for in part by interaction or competition among a number of transcription factors of these genes. Finally, the requirement of these factors might depend on the cell type.

Although IRF-2 deficient mice are viable and possess no apparent abnormalities in their behavior and reproductive ability, they manifest physical vulnerability, especially after LCMV infection. In fact, other physical vulnerabilities in the mutant mice have been consistently observed, especially in females after giving birth and in old mice, as compared to wild type and IRF-1 deficient mice.

These phenotypes most likely are the direct or indirect result of the enhanced effects of transcriptional activators such as IRF-1. In other words, the balance between activator and repressor may be impaired in this mutant mouse, and this imbalance may affect various physiological systems. In fact, overexpression of IRF-2 induces transformation of NIH3T3 cells and this phenotype is reversible by concomitant expression of IRF-1 (Harada et al., 1993). The importance of a balance between IRF-1 and IRF-2 is also revealed by the observations that (1) B cell development is inhibited in mice carrying the Eμ enhancer-IRF-1 transgene (Yamada et al., 1991), (2) deletion of IRF-1 gene is commonly found in human leukemic and preleukemic myelodysplasia (Willman et al., 1993), and (3) depletion of IRF-1 with antisense-oligonucleotides suppresses the differentiation of the macrophage cell line, M1 (Abdollahi et al., 1991). Hence, it is reasonable to speculate that in IRF-2 deficient mice cell growth and differentiation may be dysregulated by an unopposed action of IRF-1 resulting from the loss of IRF-2. Furthermore, IRF-1 is inducible by various cytokines and hormones including IFN-α/β, IFN-γ, TNF, IL-1, IL-6, LIF and prolactin (Fujita et al., 1989b; Pine et al., 1990; Yu-Lee et al., 1990; Abdollahi et al., 1991). Therefore, this imbalance will be enhanced in situations where such cytokines and hormones are produced (for example, vital infection). As an alternate model, IRF-2 may have functions other than antagonizing IRF-1, and type I IFN regulation may be more complicated than was first thought. In this context, another transcription factor with IRF-1 activity may exist that may be involved in the balance against IRF-2, becoming more functional in the absence of IRF-2.

IRF-2 deficient mice possessed alterations in haematopoietic cell populations. A large reduction in the number of LPS-responsive CFU-B in bone marrow cells was observed. Since this population mainly includes mature B cells, this is consistent with the results of flow cytometric analysis of bone marrow cells. As well, mutant mice showed a reduction of colony forming cells corresponding to multipotential progenitors, pre-B cells, and macrophage precursors. One explanation for this phenotype could be that growth and/or differentiation suppression in bone marrow of mutant mice is caused by the enhanced effects of IRF-1. Consistent with this argument, previous studies have demonstrated that IFN can suppress colony formation of various bone marrow progenitors including multipotential progenitors and granulocyte/macrophage precursors (Klimpel et al., 1982; Broxmeyer et al. 1983). Indeed, IFN is detectable in normal bone marrow (Shah et al., 1983; Zoumbos, 1985) and inducible by cytokines that affect haematopoietic differentiation (Moore et al., 1983; De Maeyer and De Maeyer-Guignard, 1988; Vilcek, 1990). In addition, bone marrow suppression is a known side effect of the clinical administration of IFNs. Hence, IRF-2 may be an important regulator of haematopoiesis, balancing the extent of bone marrow cell growth and differentiation.

Striking phenotypes were also observed after infection with LCMV, a virus known to be an excellent type I IFN inducer (Merigan et al., 1977). This is understandable, as virus infection induces various cytokines known to induce the expression of IRF-1, an imbalance between IRF-1 and IRF-2 may be enhanced, resulting in more dramatic phenotypes than the uninfected mice. In wild type mice, LCMV infection causes a transient reduction in the number of B and T lymphocytes in peripheral blood and reduction of haematocrit values. In IRF-2 deficient mice, the reduction was enhanced and prolonged in B lymphocyte and erythrocyte populations. It has long been known that LCMV induces suppression of bone marrow colony formation, which is suspected, at least in part, to be due to the action of IFN (Buchmeier et al., 1980). As described above, immunoglobulin-enhancer driven IRF-1 transgenic mice develop severe B cell lymphopenia (Yamada et al., 1991), an observation consistent with the above explanation for B cell lymphopenia in IRF-2 mutant mice after LCMV infection. It is also interesting that IFNs inhibit colony formation of erythrocyte precursors (Broxmeyer et al, 1983) and that enhanced IFN production is often observed in patients with aplastic anemia (Zoumbos et al., 1985).

IRF-2 deficient mice showed high lethality after LCMV infection, although these mice showed CTL activities and they can clear LCMV. This was also confirmed by evidence that LCMV could not be detected in moribund and postmortem mutant mice. In addition, LCMV is a noncytopathic virus (Lehmann-Grube, 1982). Taken together, LCMV is unlikely to be directly lethal. In special strains of mice, it is known that extraneural inoculation of LCMV causes LCMV-disease (Lehmann-Grube, 1982), in which LCMV-specific CTLs are involved in disease progression (Buchmeier at al., 1980; McChesney and Oldstone, 1987). Therefore, one possibility is that immunopathological reaction may be dysregulated and result in lethality. Further studies will be required to clarify this observation.

Experimental Procedures

Construction of Targeting Vector

Genomic DNA corresponding to the IRF-2 locus was isolated from a library of DBA/2 mouse DNA, using the 260bp KpnI-EcoRI fragment derived from pMIRF2–5 (Harada et al., 1989) as a probe. Restriction sites and exons were mapped by Southern blot analysis and PCR. The boundaries of exons shown in FIG. 1 were determined by sequence analysis. The plasmid pMIRF2neoEVB was constructed by ligating the following three DNA fragments: the 1.1 kb XhoI-HincII pMC1neoPolA cassette (Thomas and Capecchi, 1987), the 400bp EcoRV-EcoRI fragment containing a part of the third intron and a part of the fourth exon, a and a pBluescript SK(+) vector cleaved with SalI and EcoRI. The 3.9 kb SalI fragment containing a part of the second intron was inserted into XhoI site of the pMIRF2neoEVB. The resulting targeting vector was designated as pMIRF2neoB, containing 3.9 kb of 5'-end and 0.4 kb of 3'-end homology with the endogenous gene and neomycin resistance gene in the same transcriptional direction as the IRF-2 gene.

Transfection and Selection of Mutant ES cells

D3 ES cells (Doetschman et al., 1985) were maintained in the undifferentiated state in Dulbecco's modified Eagle's medium (DMEM) supplemented with 15% fetal calf serum, $5 \times 10^{-5}$M 2-mercaptoethanol, antibiotics and LIF. Electropotation of ES cells, selection of G418-resistant colonies, and PCR screening for homologous recombination were carried out as described (Joyner et al., 1989). The following two primers were used for the detection of homologous recombination events: neo. 5'-AACGCACGGGTGTTGGGTCGTTTG-3', IRF-2. 5'-CGGTAGACTCTGAAGGCGTTGTT-3'. PCR was performed for 40 cycles using a thermal cycler (Perkin Elmer Cetus) and the following reaction conditions: denaturing temperature of 94° C. for 30 seconds, annealing temperature of 60° C. for 30 seconds and elongation temperature of 72° C. for 2 minutes. Homologous recombination was subsequently confirmed by genomic Southern blot analysis.

Generation of Mutant Mice

The protocol used was essentially as described elsewhere (Robertson, 1987; Bradley, 1987). In brief, mutant cell lines were injected into blastocysts flushed from the uteri and oviducts of 3.5 day post coital (p.c.) C57BL/6J mice. Injected blastocysts were transferred into the uterus of 2.5 day p.c. pseudopregnant CD1 recipient mice. Chimaeras were bred with B6D2F1/J or C57BL/6J. Agouti offsprings were checked for the presence of the mutation by Southern blot analysis. Homozygous mice were generated by intercross of heterozygous mice.

Gel Shift Analysis

Gel shift analysis was performed as previously described (Harada et al., 1990).

Northern Blot Analysis

Northern blot analysis was performed as previously described (Harada et al., 1990). To prepare probes, the following DNAs were labeled by the multiprime DNA labeling reaction (Amersham): 2'-5'OAS, a 1.4 kb EcoRI fragment from pMA25 (Yoshitake et al., 1986); 1–8, 0.2 kb EcoRI-HindIII fragment from Mu 1–8 (Flenniken et al., 1988); PKR, 1.0 kb EcoRI-BamHI fragment from murine p65 kinase cDNA (Feng et al., 1992); IFN-α, IFN-β, and β-actin probes, which are the same as described previously (Miyamoto et al., 1988).

Flow Cytometric Analysis

Thymus, spleen, lymph nodes, bone marrow, peripheral blood, and peritoneal cells were prepared from 6 to 9 week old mice unless otherwise noted. Single cell suspensions were stained with monoclonal antibodies on ice for 30 min in phosphate buffered saline (PBS) containing 1% bovine serum albumin and 0.1% sodium azide, and analysed by double colour flow cytometry on a FACScan (Becton Dickinson). Monoclonal antibodies used were FITC-, biotin-, or phycoerythin-conjugated antibodies against Thy1.2 (53-2.1), CD3-ε chain (145-2C11), Ly-5 (B220; RA3-6B2), IgM (R-40-97), Ly-2 (53-6.7), Ly-3 (53-5.8), L3T4 (RM-4-5), Pgp-1 (1M7), heat stable antigen (J11d), TcRαβ (H57-597), TcRγδ (GL3) and H-2K$^b$ (AF6-88.5). Biotinylated antibodies were followed by streptoavidin. All monoclonal antibodies were purchased from PharMingen Inc.

Cytotoxic Asssy and Titration of virus

Two hundred plaque forming units of LCMV (Armstrong strain) were injected intravenously into 6 to 12 week old IRF-2 wild type and homozygous mutant mice. At day 8 after infection, spleen cells were assayed for LCMV-specific cytotoxic T cell in a standard $^{51}$Cr release assay as described in detail elsewhere (Pircher et al., 1987; Ohashi et al., 1991).

To determine the viral titer, spleen homogenates were prepared at day 3, 6 and 15 after inoculation. Liver and spleen homogenates were prepared from moribund or postmortem mutant mice as well. These homogenates were subjected to the assay system previously described (Battegay et al., 1991). Briefly, serially diluted homogenates were added to the target cell line MC57G. After 2 days incubation at 37° C. plaques were detected by an indirect immunostaining method using the anti-LCMV monoclonal antibody VL-4.

Immunoglobulin Isotyping

Sera were prepared from 6 week old homozygous mice and sex/age matched wild type or heterozygous mice and diluted 100 times in PBS. The immunoglobulin isotypes were determined by a panel of mouse isotype specific antibodies (Bio-Rad), according to the manufacturer's protocol.

Colony Formation Assay

Essential aspects of this assay system were described in detail elsewhere (Paige and Skarvall, 1982; Paige et al., 1984). In brief, bone marrow or spleen cells ($10^4$ or $5 \times 10^3$) were cultured with OPTI-MEM (Gibco, Grand Island, N.Y.) containing 0.3% agar and stimulators described in FIG. 18 with or without the stromal cell line S17 (Narendran et al., 1992). After 5–7 days of incubation, colonies were counted using a dissecting microscope. Concentration of reagents used were 25 µg/ml for LPS and 100U/ml for IL-7. IL-3 and CSF-1 were prepared from the supernatant of cells carrying IL-3 and CSF-1 expression vectors and used at titrated optimum concentration.

Deposits

The ES cell line having the disrupted IRF-2 gene as shown in FIG. 1 has been deposited in the American Type Culture Collection, Rockville, Md., and given ATCC Accession No. CRL 11383.

REFERENCES:

Abdollahi, A. K., Lord, B., Hoffman-Liebermann, and Liebermann, D. A. (1991). Interferon regulatory factor-1 is a myeloid differentiation primary response gene induced by interleukin 6 and leukemia inhibitory factor: role in growth inhibition. Cell Growth Differ. 2, 401–407.

Battegay, M., Cooper, S., Althage, A., Baenziger, J., Hengartner, H., and Zinkernagel, R. M. (1991). Quantification of lymphocytic choriomeningitis virus with an immunological focus assay in 24- or 96-well plates. J. Virol. Meth. 33, 191–198.

Blank, V., Kourilsky, P., and Israel, A. (1992). NF-κB and related proteins: Rel/dorsal homologies meet ankyrin-like repeats. TIBS 17, 135–140.

Bradley, A. (1987). Production and analysis of chimaeric mice. In Teratocarcinomas and Embryonic Stem Cells, E. J. Robertson, ed. (Oxford, Washington, D.C.: IRL Press), pp113–152.

Broxmeyer, H. E., Lu, L., Platzer, E., Fiet, C., Juliano, L., and Rubin, B. Y. (1983). Comparative analysis of the influences of human gamma, alpha, and beta interferons on human multipotential (CFU-GEMM), erythroid (BFU-E), and granulocyte-macrophage (CFU-GM) progenitor cells. J. Immunol. 131, 1300–1305.

Buchmeier, M. J., Welsh, R. M., Dutko, F. J., and Oldstone, M. B. A. (1980). The virology and immunobiology of lymphocytic choriomeningitis virus infection. Adv. in Immunol. 30, 275–331.

Capecchi, M. R. (1989). Altering the genome by homologous recombination. Science 244, 1288–1292.

De Maeyer, E., and De Maeyer-Guignard, J. (1988). Interferons and other regulatory cytokines. (New York: John Wiley & Sons).

Doetschman, T. C., Eistelter, H., Katz, M., Schmidt, W., and Kemler, R. (1985). The in vitro development of blastocyst-derived embryonic stem cell lines: formation of visceral yolk sac, blood islands and myocardium. J. Embryol. Exp. Morphol. 87, 27–45.

Driggers, P. H., Ennist, D. L., Gleason, S. L., Mak, W.-H., Marks, M. S., Levi, B.-Z., Flanagan, J. R., Appella, E., and Ozato, K. (1990). An interferon-regulated protein that binds the interferon-inducible enhancer element of major histocompatibility complex class I genes. Proc. Natl. Acad. Sci. USA 87, 3743–3747.

Feng, G.-S., Chong, K., Kumar, A., and Williams, B. R. G. (1992). Identification of double-stranded RNA-binding domains in the interferon-induced double-stranded RNA-activated p68 kinase. Proc. Natl. Acad. Sci. USA 89, 5447–5451.

Flenniken, A., Galabru, J., Rutherford, M. N., Hovanessian, A. G., and Williams, B. R. G. (1988). Expression of interferon-induced genes in different tissues of mice. J. Virol. 62, 3077–3083.

Fujita, T., Ohno, S., Yasumitsu, H., and Taniguchi, T. (1985). Delimitation and properties of DNA sequences required for the regulated expression of human interferon-γ gene. Cell 41, 489–496.

Fujita, T., Shibuya, H., Hotta, H., Yamanishi, K. and Taniguchi, T. (1987). Interferon-γ gene regulation: tandemly repeated sequences of a synthetic 6bp oligomer function as virus-inducible enhancer. Cell 49, 357–367.

Fujita, T., Sakakibara, J., Sudo, Y., Miyamoto, M., Kimura, Y., and Taniguchi, T. (1988). Evidence for a nuclear factor(s), IRF-1, mediating induction and silencing properties to human IFN-8 gene regulatory elements. EMBO J. 7, 3397–3405.

Fujita, T., Kimura, Y., Miyamoto, M., Barsoumian, E. L., and Taniguchi, T. (1989a). Induction of endogenous IFN-α and IFN-β genes by a regulatory transcription factor, IRF-1. Nature 337, 270–272.

Fujita, T., Reis, L., Watanabe, N., Kimura, Y., Taniguchi, T., and Vilček, J. (1989b). Induction of the transcription factor IRF-1 and interferon-β mRNAs by cytokines and activators of second messenger pathways. Proc. Natl. Acad. Sci. USA 86, 9963–9940.

Harada, H., Fujita, T., Miyamoto, M., Kimura, Y., Maruyama, M., Furia, A., Miyata, T., and Taniguchi, T. (1989). Structurally similar but functionally distinct factors, IRF-1 and IRF-2, bind to the same regulatory elements of IFN and IFN-inducible genes. Cell 58, 729–739.

Harada, H., Willison, K., Sakakibara, J., Miyamoto, M., Fujita, T., and Taniguchi, T. (1990). Absence of type I interferon system in EC cells: transcriptional activator (IRF-1) and repressor (IRF-2) genes are developmentally regulated. Cell 63, 303–312.

Harada, H., Kitagawa, M., Tanaka, N., Yamamoto, H., Harada, K., Ishihara, M.,and Taniguchi, T. (1993). Antioncogenic and oncogenic potentials of transcriptional regulators IRF-1 and -2. Science 259, 971–974.

Hogan, B., Costantini, F., and Lacy, E. (1986). Manipulating the Mouse Embryo: A Laboratory Manual (Cold Spring Harbor, New York: Cold Spring Harbor Laboratory).

Joyner, A., Skarnes, W. C., and Rossant, J. (1989). Production of a mutation in mouse En-2 gene by homologous recombination in embryonic stem cells. Nature 338, 153–155.

Karin, M., and Smeal, T. (1992). Control of transcription factors by signal transduction pathways: the beginning of the end. TIBS 17, 418–422.

Keller, A.D. and Maniatis T. (1991). Identification and characterization of a novel repressor of interferon-β gene expression. Genes Dev. 5, 868–879.

Klimpel, G. R., Fleischmann, W. R. Jr., and Klimpel, K. D. (1982). Gamma interferon and IFNα/β suppress murine myeloid colony formation (CFU-C): magnitude of suppression is dependent upon level of colony-stimulating factor (CSF). J. Immunol. 129, 76–80.

Lehmann-Grube, F. (1982). Lymphocytic choriomeningitis virus. The mouse in biomedical research, Vol.II, Diseases, H. L. Foster, D. Small, and J. D. Fox, eds. (New York: Academic Press), pp.231–266.

MacDonald, N. J., Kuhl, D., Maguire, D., Näf, D., Gallant, P., Goswamy, A., Hug, H., Bueler, H., Chaturvedi, M., de la Fuente, J., Ruffner, H., Meyer, F., and Weissmann, C. (1990). Different pathways mediate virus inducibility of the human IFN-α1 and IFN-β genes. Cell 60, 767–779.

Marcu, K. B., Bossone, S. A., and Patel, A. J. (1992). myc function and regulation. Annu. Rev. Biochem. 61, 809–860.

McChesney, M. B., and Oldstone, M. B. A. (1987). Viruses perturb lymphocyte functions: Selected principles characterizing virus-induced immunosuppression. Annu. Rev. Immunol. 5, 279–304.

Merigan, T. C., Oldstone, M. B. A., and Welsh, R. M. (1977). Interferon production during lymphocytic choriomeningitis virus infection of nude and normal mice. Nature 268, 67–68.

Miyamoto, M., Fujita, T., Kimura, Y., Maruyama, M., Harada, H., Sudo, Y., Miyata, T., and Taniguchi, T. (1988). Regulated expression of a gene encoding a nuclear factor, IRF-1, that specifically binds to IFN-beta gene regulatory elements. Cell 54, 903–913.

Moore, R. N., Larsen, H. S., Horohov, D. W., and Rouse, B. T. (1983). Endogenous regulation of macrophage proliferative expansion by colony-stimulating-factor-induced interferon. Science 223, 178–181.

Näf, D., Hardin, S. E., and Weissmann, C. (1991). Multimerization of AAGTGA and GAAAGT generates sequences that mediate virus inducibility by mimicking an interferon promoter element. Proc. Natl. Acad. Sci. USA 88, 1369–1373.

Narendran, A., Cumano, A., Dorshkind, K., and Paige, C. J. (1992). The stromal cell line S17 supports the growth of lipopolysaccharide-stimulated CBA/N spleen colonies in vitro. Eur. J. Immunol. 22, 1001–1006.

Nelson, N., Marks, M. S., Driggers, P. H., and Ozato, K. (1993). Interferon consensus sequence-binding protein, a member of the Interferon Regulatory Factor family, supresses interferon-induced gene transcription. Mol. Cell. Biol. 13, 588–599.

Ohashi, P.S., Oehen, S., Buerki, K., Pircher, H., Ohashi, C. T., Odermatt, B., Malissen, B., Zinkernagel, R. M., and Hengartner, H. (1991). Ablation of "tolerance" and induction of diabetes by virus infection in viral antigen transgenic mice. Cell 65, 305–317.

Paige, C. J., and Skarvall, H. (1982). Plaque formation by B cell colonies. J. Immunol. Meth. 52, 51–61.

Paige, C. J. (1983). Surface immunoglobulin-negative B-cell precursors detected by formation of antibody-secreting colonies in agar. Nature 302, 711–713.

Pine, R., Levy, D. E., Reich, N., and Darnel, J. E., Jr. (1990). Purification and cloning of interferon-stimulated gene factor 2 (ISGF2): ISGF2 (IRF-1) can bind to the promoters of both beta interferon and interferon-stimulated genes but not a primary transcriptional activator. Mol. Cell. Biol. 10, 2448–2457.

Pircher, H. P., Baenziger, J., Schilham, M., Sado, T., Kamisaku, H., Hengartner, H., and Zinkernagel, R. M. (1987). Characterization of virus-specific cytotoxic T cell clones from allogenic bone marrow chimeras. Eur. J. Immunol. 17, 159–166.

Pleiman, C. M., Gimpel, S. D., Park, L. S., Harada, H., Taniguchi, T., and Ziegler, S. F. (1991). Organization of the murine and human interleukin-7 receptor genes: two mRNAs generated by differential splicing and presence of a type I interferon-inducible promoter. Mol. Cell. Biol. 11, 3052–3059.

Reis, L. F., Harada, H., Wolchok, J. D., Taniguchi, T., and Vilček, J. (1992). Critical role of a common transcription factor, IRF-1, in the regulation of IFN-β and IFN-inducible genes. EMBO J. 11, 185–193.

Robertson, E. J. (1987). Embryo-derived stem cell lines in Teratocarcinomas and Embryonic Stem Cells. E. J. Robertson, ed. (Oxford, Washington, D.C.: IRL Press), pp71–112.

Shah, G., Dexter, T. M., and Lanotte, M. (1983). Interferon production by human bone marrow stromal cells. Br. J. Haematol. 54, 365–372.

Stark, G. R., and Kerr, I. M. (1992). Interferon-dependent signaling pathways: DNA elements, transcription factors, mutations, and effects of viral proteins. J. Interferon Res. 12, 147–151.

Tanaka, N. and Taniguchi, T. (1992). Cytokine gene regulation: regulatory cis-elements and DNA binding factors involved in the interferon system. Adv. in Immunol. 52, 263–281.

Tanaka, N., Kawakami, T., and Taniguchi, T. (1993). Recognition DNA sequences of interferon regulatory factor-1 (IRF-1) and IRF-2, regulators of cell growth and interferon system. Mol. Cell. Biol. in press.

Taniguchi, T. (1988). Regulation of cytokine gene expression. Annu. Rev. Immunol. 6, 439–464.

Thomas, K. R., and Capecchi, M. R. (1987). Site-directed mutagenesis by gene targeting in mouse embryo-derived stem cells. Cell 51, 503–512.

Uegaki, K., Shirakawa, M., Fujita, T., Taniguchi, T., and Kyogoku, Y. (1993). Characterization of the DNA binding domain of the mouse IRF-2 protein. Protein Engineering 6, 195–200.

Veals, S. A., Schindler, C., Leonard, D., Fu, X.-Y., Aebersold, R., Darnell, J. E., Jr. and Levy, D. E. (1992). Subunit of an alpha-interferon-responsive transcription factor is related to interferon regulatory factor and Myb families of DNA-binding proteins. Mol. Cell. Biol. 12, 3315–3324.

Vilček, J. (1990). Interferons. In Peptide Growth Factors and Their Receptors, Handbook of experimental pharmacology, M. A. Sporn and A. B. Roberys, eds. (Berlin: Springer-Varlag), pp. 3–38.

Weisz, A., Marx, P., Sharf, R., Appella, E., Driggers, P. H., Ozato, K., and Levi, B-Z. (1992). Human interferon consensus sequence binding protein is a negative regulator of enhancer elements common to Interferon-inducible genes. J. Biol. Chem. 267, 25589–25596.

Willman, C. L., Sever, C. E., Pallavicini, M. G., Harada, H., Tanaka, N., Slovak, M. L., Yamamoto, H., Harada, K., Meeker, T. C., List, A. F., and Taniguchi, T. (1993). Deletion of IRF-1, mapping to chromosome 5q31.1, in human leukemia and preleukemic myelodysplasia. Science 259, 968–971.

Yamada, G., Ogawa, M., Akagi, K., Miyamoto, H., Nakano, N., Itoh, S., Miyazaki, J.-I., Nishikawa, S.-I., Yamamura, K., and Taniguchi, T. (1991). Specific depletion of the B-cell population induced by aberrant expression of human interferon regulatory factor 1 gene in transgenic mice. Proc. Natl. Acad. Sci. USA 88, 532–536.

Yoshitake, L, Fukunaga, R., Shiojiri, S., and Sokawa, Y. (1986). Mouse 2–5A synthetase cDNA: nucleotide sequence and comparison to human 2–5A synthetase. Nucl. Acids Res. 14, 10117.

Yu-Lee, L.-Y., Hrachovy, J. A., Stevens, A. M., and Schwartz, L. A. (1990). Interferon regulatory factor 1 is an intermediate-early gene under transcriptional regulation by prolactin in Nb2 T cells. Mol. Cell. Biol. 10, 3087–3094.

Zoumbos, N. C., Garcon, P., Djeu, J. Y, and Young, N. S. (1985). Interferon is a mediator of hematopoietic suppression in aplastic anemia in vitro and in vivo. Proc. Natl. Acad. Sci. USA 82, 188–192.

We claim:

1. A mutant mouse comprising disrupted alleles of the Interferon Regulatory Factor-2 (IRF-2) gene, the disruption being introduced into the mouse or an ancestor of the mouse at an embryonic stage, wherein the disruption prevents the synthesis of functional IRF-2 in cells of the mouse and results in the mutant mouse having an increased susceptibility to infection by lymphocytic choriomeningitis virus (LCMV) relative to the LCMV susceptibility of a mouse comprising an undisrupted IRF-2 gene.

2. The mouse of claim 1 wherein the disruption comprises the deletion of exon 3 of the IRF-2 gene.

3. An embryonic stem cell line comprising a disrupted IRF-2 gene and having ATCC Accession No. CRL 11383.

4. A mutant mouse comprising disrupted alleles of the IRF-2 gene, the disruption being introduced into the mouse or an ancestor of the mouse at an embryonic stage using an embryonic stem cell line having ATCC Accession No. CRL 11383, wherein the disruption prevents the synthesis of functional IRF-2 in cells of the mouse and results in the mutant mouse having an increased susceptibility to infection by LCMV relative to the LCMV susceptibility of a mouse comprising an undisrupted IRF-2 gene.

* * * * *

UNITED STATES PATENT AND TRADEMARK OFFICE
CERTIFICATE OF CORRECTION

PATENT NO. : 5,675,059
DATED : October 17, 1997
INVENTOR(S) : Mak et al.

Page 1 of 1

It is certified that error appears in the above-identified patent and that said Letters Patent is hereby corrected as shown below:

Title page,
Item [56], please delete "T. Mauiatis" and insert -- T. Maniatis -- therefor.

Column 6,
Line 12, please delete "embryohal" and insert -- embryonal -- therefor.

Column 11,
Line 10, please delete "a" first occurrence.

Column 12,
Line 16, please delete "Asssy" and insert -- Assay --, therefor.

Signed and Sealed this

Twenty-first Day of May, 2002

Attest:

Attesting Officer

JAMES E. ROGAN
Director of the United States Patent and Trademark Office